US010068060B2

(12) United States Patent
Madan et al.

(10) Patent No.: US 10,068,060 B2
(45) Date of Patent: Sep. 4, 2018

(54) METHOD FOR MODELING BEHAVIOR AND PSYCHOTIC DISORDERS

(71) Applicant: Ginger.io, Inc., San Francisco, CA (US)

(72) Inventors: Anmol Madan, San Francisco, CA (US); Sai Moturu, San Francisco, CA (US); Karim Wahba, San Francisco, CA (US); Shishir Dash, San Francisco, CA (US); Gourab De, San Francisco, CA (US)

(73) Assignee: Ginger.io, Inc., San Francisco, CA (US)

( * ) Notice: Subject to any disclaimer, the term of this patent is extended or adjusted under 35 U.S.C. 154(b) by 468 days.

(21) Appl. No.: 14/839,232

(22) Filed: Aug. 28, 2015

(65) Prior Publication Data

US 2015/0370994 A1 Dec. 24, 2015

Related U.S. Application Data

(63) Continuation-in-part of application No. 13/969,339, filed on Aug. 16, 2013.
(Continued)

(51) Int. Cl.
*G06F 19/00* (2018.01)
*G16H 50/50* (2018.01)
*G16H 10/20* (2018.01)

(52) U.S. Cl.
CPC ...... *G06F 19/3437* (2013.01); *G06F 19/3418* (2013.01); *G16H 10/20* (2018.01); *G16H 50/50* (2018.01); *G06F 19/3456* (2013.01)

(58) Field of Classification Search
None
See application file for complete search history.

(56) References Cited

U.S. PATENT DOCUMENTS 7,188,151 B2 3/2007 Kumar et al.
7,248,677 B2 7/2007 Randall et al.
(Continued)

FOREIGN PATENT DOCUMENTS

CN 101600008 A 12/2009
WO 2008085308 A1 7/2008
(Continued)

*Primary Examiner* — Michael Tomaszewski
(74) *Attorney, Agent, or Firm* — Jeffrey Schox; Brian Lao

(57) ABSTRACT

A method and system for modeling behavior and a psychotic disorder-related state of a patient, the method comprising: receiving a log of use dataset associated with communication behavior of the patient during a time period; receiving a supplementary dataset characterizing mobility-behavior of the patient during the time period; generating a predictive model based upon a passive dataset derived from the log of use dataset and the supplementary dataset; transforming at least one of the passive dataset and an output of the predictive model into an analysis of a psychotic episode-risk state of the individual associated with at least a portion of the time period; and upon detection that parameters of the psychotic episode-risk state satisfy at least one threshold condition, automatically initiating provision of a therapeutic intervention for the individual by way of at least one of the computing system and the mobile communication device.

20 Claims, 6 Drawing Sheets

Related U.S. Application Data

(60) Provisional application No. 61/683,867, filed on Aug. 16, 2012, provisional application No. 61/683,869, filed on Aug. 16, 2012, provisional application No. 62/043,248, filed on Aug. 28, 2014, provisional application No. 62/085,726, filed on Dec. 1, 2014.

(56) References Cited

U.S. PATENT DOCUMENTS

| | | |
|---|---|---|
| 7,761,309 B2 | 7/2010 | Sacco et al. |
| 2004/0225340 A1 | 11/2004 | Evans |
| 2005/0108051 A1 | 5/2005 | Weinstein |
| 2007/0094048 A1* | 4/2007 | Grichnik ............... G06Q 50/22 705/2 |
| 2007/0226012 A1 | 9/2007 | Salgado et al. |
| 2007/0288266 A1 | 12/2007 | Sysko et al. |
| 2009/0125333 A1 | 5/2009 | Heywood et al. |
| 2010/0082367 A1* | 4/2010 | Hains ................. G06F 19/3456 705/2 |
| 2010/0203876 A1 | 8/2010 | Krishnaswamy |
| 2011/0009715 A1 | 1/2011 | Karplus et al. |
| 2011/0066036 A1 | 3/2011 | Zilca et al. |
| 2011/0184250 A1 | 7/2011 | Schmidt et al. |
| 2013/0117040 A1 | 5/2013 | James et al. |
| 2013/0297536 A1* | 11/2013 | Almosni ............... G16H 50/20 706/12 |
| 2014/0039914 A1 | 2/2014 | Dansereau et al. |

FOREIGN PATENT DOCUMENTS

| | | |
|---|---|---|
| WO | 2008096634 A1 | 8/2008 |
| WO | 2012025622 A2 | 3/2012 |
| WO | 2015003247 A1 | 1/2015 |

* cited by examiner

METHOD FOR MODELING BEHAVIOR AND PSYCHOTIC DISORDERS

CROSS-REFERENCE TO RELATED APPLICATIONS

This application is a continuation-in-part application of U.S. application Ser. No. 13/969,339 filed 16 Aug. 2013, which claims the benefit of U.S. Provisional Application Ser. No. 61/683,867 filed on 16 Aug. 2012 and U.S. Provisional Application Ser. No. 61/683,869 filed on 16 Aug. 2012, which are each incorporated in its entirety herein by this reference.

This application also claims the benefit of U.S. Provisional Application Ser. No. 62/043,248 filed 28 Aug. 2014, and U.S. Provisional Application Ser. No. 62/085,726 filed 1 Dec. 2014, which are each incorporated in its entirety herein by this reference.

TECHNICAL FIELD

This invention relates generally to the field of patient health and more specifically to a new and useful method for modeling behavior and psychosis in the field of patient health.

BACKGROUND

Schizophrenia spectrum and psychotic disorders (as described, for instance, in editions of the Diagnostic and Statistical Manual of Mental Disorders) are characterized by a combination of symptoms that interfere with a person's ability to interact with society, work effectively, sleep, and maintain physical health. Psychosis is characterized by a loss of connection with reality (e.g., including hallucinations and delusions). Early intervention in psychosis is crucial to affecting patient outcomes, due to the rapid progression from stable to instable states. However, early intervention requires intensive patient assessment and monitoring. Current systems and methods for monitoring patients exhibiting symptoms of psychosis can influence patient outcomes, but are typically time and/or cost-intensive or entirely fail to identify when a patient is entering a critical state of psychosis at which intervention would be most effective. As such, current standards of detection, diagnosis and treatment of psychotic disorders, as well as barriers (e.g., social barriers) to seeking diagnosis and treatment, are responsible for delays in diagnoses of disorders and/or misdiagnoses of disorders, which cause psychotic disorders to remain untreated. Furthermore, such standards result in a reactionary approach, as opposed to a preventative approach to a psychosis-related event. Even further, changes in psychotic state can go undetected, resulting in regressions in psychotic state, patient harm (e.g., self-inflicted or outwardly afflicted), or even death. While the delays can be due to the sensitive nature of such disorders, current standards of detection diagnosis are severely deficient in many controllable aspects. In addition to these deficiencies, further limitations in detection, diagnosis, treatment, and/or monitoring of patient progress during treatment prevent adequate care of patients with diagnosable and treatable psychotic disorders.

As such, there is a need in the field of patient health for a new and useful method for modeling behavior and psychosis. This invention creates such a new and useful method for modeling behavior and psychosis.

DESCRIPTION OF THE EMBODIMENTS

The following description of the embodiments of the invention is not intended to limit the invention to these embodiments, but rather to enable any person skilled in the art to make and use this invention.

1. Method

Figure 1:
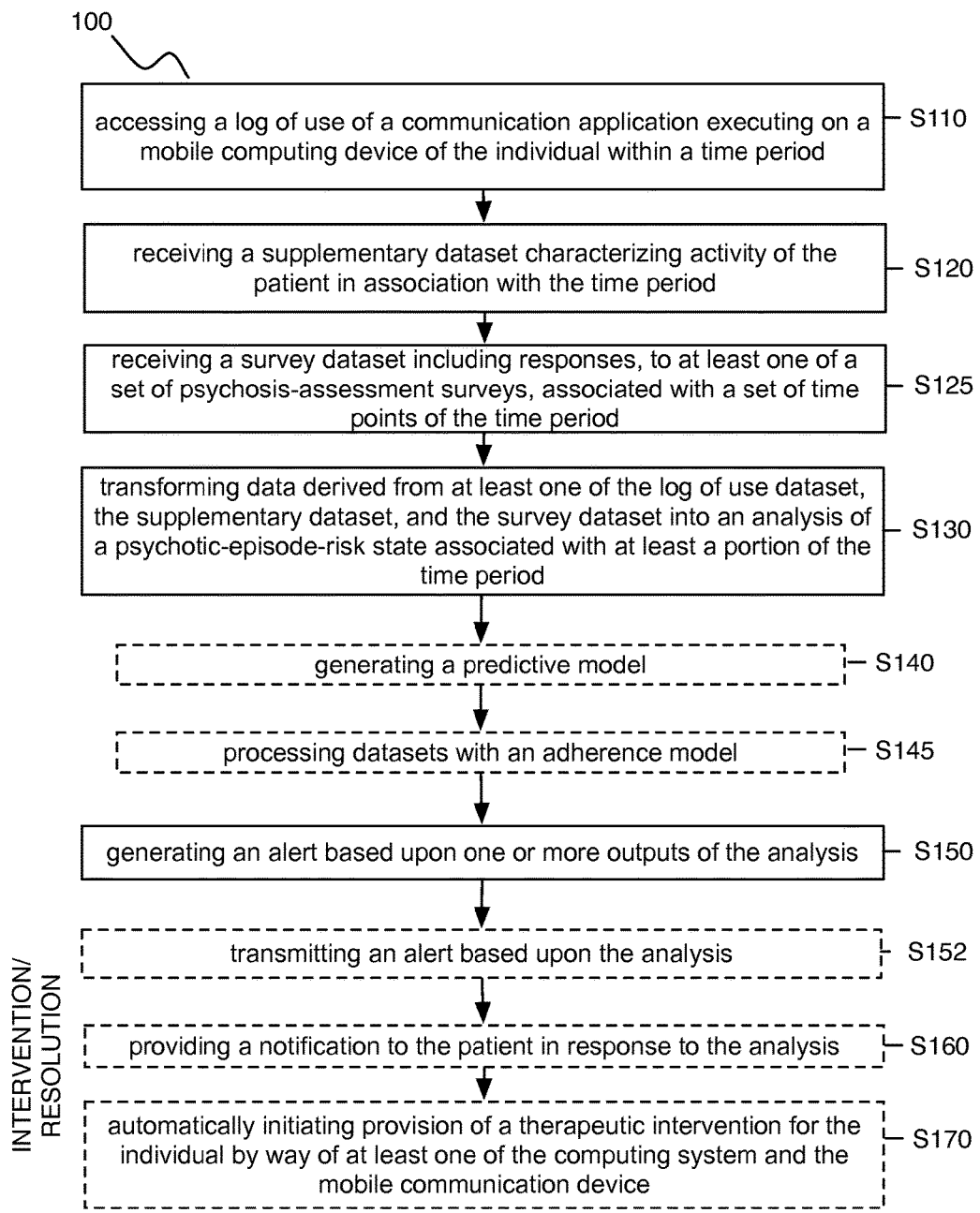
FIG. 1 is a flowchart of an embodiment of a method for modeling behavior and psychosis.

As shown in FIG. 1, a method 100 for modeling behavior and psychosis of a patient includes: receiving a log of use dataset of a communication module executing on a mobile computing device by the patient during a time period S110; receiving a supplementary dataset characterizing mobility-behavior of the patient in association with the time period S120; receiving a survey dataset including responses, to at least one of a set of psychosis-assessment surveys, associated with a set of time points of the time period, from the patient S125; transforming data derived from at least one the log of use dataset, the supplementary dataset, and the survey dataset into an analysis of a psychotic episode-risk state associated with at least a portion of the time period S130; and generating an alert based upon one or more outputs of the analysis S150. In some variations, the method 100 can further include any one or more of: providing a notification to the patient, at the mobile communication device, in response to the analysis S160; and automatically initiating provision of a therapeutic intervention for the individual by way of at least one of the computing system and the mobile communication device S170.

The method 100 functions to analyze communication behavior and other information regarding a patient (e.g., user, at-risk individual) exhibiting symptoms of psychosis, in order to assess risk of the patient in entering an adverse psychotic state (e.g., hallucinations, delusions). As such, the method 100 can facilitate monitoring of states of psychosis in a patient exhibiting symptoms of psychosis, by enabling detection of changes in the patient's condition. In a specific application, the method 100 can monitor and analyze communication behavior, mobility behavior, and/or other behavior detected from any other suitable sensor(s) associated with a patient with a psychotic disorder over time, and provide an alert to a caretaker associated with the patient and/or to the patient upon detection that the patient has entered or is at risk of entering a critical state of psychosis (e.g., self-harming or outwardly-harming state). Thus, the method 100 can provide a predictive model for one or more patients experiencing symptoms of a psychotic disorder, as well as an intervention model for providing interventions at key time points, to optimize improvement in patient outcomes (e.g., as exhibited by an improved state). The intervention model can thus implement an anticipated patient psychotic state to drive automated or manual targeted intervention for a patient (e.g., via a phone call, email, health tip notification, insight, other electronic device-based messaging, other electronic device-based notifications, or other electronic communication, etc.) in some applications. In further embodiments, an analysis of the method 100 can be used to generate and/or provide therapeutic regimens to the patient as a therapeutic measure in promoting the psychological health of the patient.

As such, the method 100 can be used to monitor and/or treat patients at risk for entering states associated with one or more schizophrenia spectrum and psychotic disorders (as described, for instance, in editions of the Diagnostic and Statistical Manual of Mental Disorders), especially for patients diagnosed with or exhibiting symptoms of any one or more of: schizophrenia, schizophreniform disorder, schizoaffective disorder, early psychosis, delusional disorder, brief psychotic disorder, catatonia, attenuated psychosis syndrome, shared psychotic disorder, psychotic disorder, substance-induced psychotic disorder, mood disorders, bipolar disorders (e.g., Bipolar I disorder, Bipolar II disorder), cyclothymic disorder, premenstrual dysphoric disorder, and any other suitable psychotic disorder. Such symptoms can include delusions, hallucinations, disorganized speech, disorganized behavior, catatonic behavior, reality distortion behavior, suicidal intent, and any other negative symptoms. In relation to psychosis and/or psychotic disorder states described below, the variations of the method 100 can thus be used to detect and improve states associated with one or more of the above schizophrenia spectrum and psychotic disorders (as described, for instance, in editions of the Diagnostic and Statistical Manual of Mental Disorders), and/or any other suitable schizophrenia spectrum and psychotic disorder.

While the method 100 can be implemented for a single patient exhibiting symptoms of psychosis, the method 100 can additionally or alternatively be implemented for a population of patients (e.g., including the entity, excluding the entity), wherein the population of patients can include patients similar to and/or dissimilar to the patient (e.g., in exhibition of symptoms of psychosis, in demographic group, in medical condition, etc.). Thus, information derived from the population of patients can be used to provide additional insight into connections between the patient's behavior and risk of entering one of a spectrum of psychotic states, due to aggregation of data from a patient population. In a specific example, the method 100 involves a population of patients between 14 and 30 years of age, each patient having a mobile computing device (e.g., smart phone, tablet, wearable computing device, etc.) and suffering from a type of psychotic disorder (e.g., a disorder along a schizophrenia spectrum, a mood disorder with psychotic features). In the specific example, the population of patients omits patients suffering from visual or hearing impairment; however, variations of the specific example can alternatively include patients of any other suitable demographic or condition.

The method 100 is preferably implemented at least in part by an embodiment of the system 200 described in Section 2 below, variations of which can be implemented at least in part by embodiments, variations, and examples of the system described in U.S. application Ser. No. 13/969,339 entitled "Method for Modeling Behavior and Health Changes" and filed on 16 Aug. 2013; however, the method 100 can alternatively be implemented using any other suitable system configured to process communication and/or other behavior of the patient, in aggregation with other information, in order to generate a model of behavior and state of psychosis in the patient.

1.1 Method—Passive Data

Block S110 recites: receiving a log of use dataset of a communication module executing on a mobile computing device by the patient during a time period, which functions to unobtrusively collect and/or retrieve communication-related data from a patient's mobile communication device. Preferably, Block S110 is implemented using a module of a computing system configured to interface with a native data collection application executing on a mobile communication device (e.g., smartphone, tablet, personal data assistant (PDA), personal music player, vehicle, head-mounted wearable computing device, wrist-mounted wearable computing device, etc.) of the patient, in order to retrieve patient communication data. As such, in one variation, a native data collection application can be installed on the mobile communication device of the patient, can execute substantially continuously while the mobile communication device is in an active state (e.g., in use, in an on-state, in a sleep state, etc.), and can record communication parameters (e.g., communication times, durations, contact entities, etc.) of each inbound and/or outbound communication (e.g., call, message) from the mobile communication device. In implementing Block S110, the mobile communication device can then upload this data to a database (e.g., remote server, cloud computing system, storage module), at a desired frequency (e.g., in near real-time, every hour, at the end of each day, etc.) to be accessed by the computing system. In one example of Block S110, the data collection application can launch on the patient's mobile communication device as a background process that gathers patient data once the patient logs into an account, wherein the patient data includes how and with what frequency the patient interacts with and communicates with other individuals through phone calls, e-mail, instant messaging, an online social network, and any other suitable mode of communication.

As such, in accessing the log of use of the native communication application and receiving the log of use dataset, Block S110 preferably enables collection of one or more of: phone call-related data (e.g., number of sent and/or received calls, call duration, call start and/or end time, location of patient before, during, and/or after a call, and number of and time points of missed or ignored calls); text messaging (e.g., SMS test messaging) data (e.g., number of messages sent and/or received, message length associated with a contact of the individual, message entry speed, delay between message completion time point and sending time point, message efficiency, message accuracy, time of sent and/or received messages, location of the patient when receiving and/or sending a message); data on textual messages sent through other communication venues (e.g., public and/or private textual messages sent to contacts of the patient through an online social networking system, reviews of products, services, or businesses through an online ranking and/or review service, status updates, "likes" of content provided through an online social networking system), vocal and textual content (e.g., text and/or voice data that can be used to derive features indicative of negative or positive sentiments) and any other suitable type of data.

Figure 2:
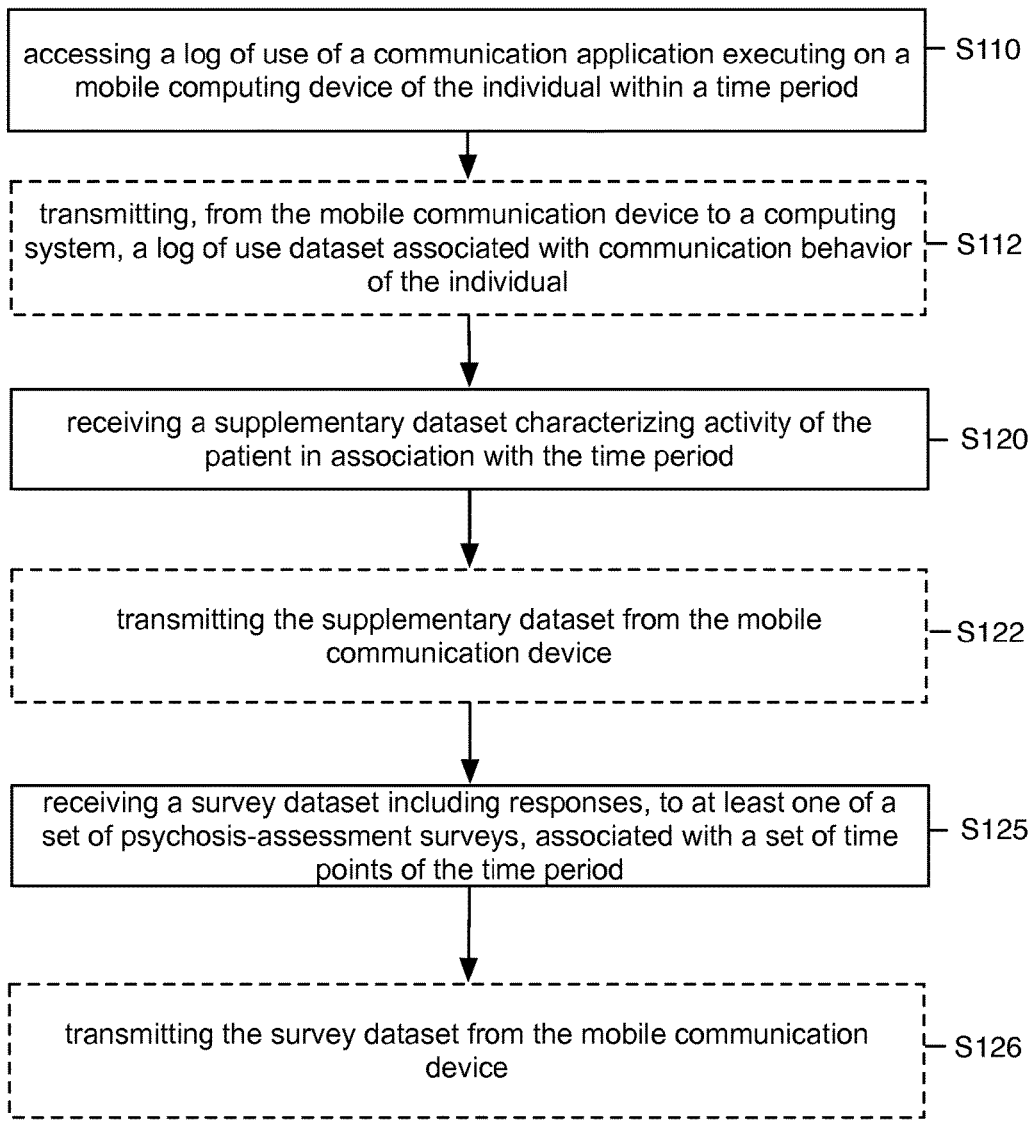
FIG. 2 depicts a flowchart of a portion of an embodiment of a method for modeling behavior and psychosis.

In relation to receiving the log of use dataset, Block S110 can include accessing the log of use at the mobile communication device of the individual, and transmitting, from the mobile communication device to a computing system, a log of use dataset associated with communication behavior of the individual S112, as shown in FIG. 2. The computing system can be implemented in one or more of a processing module of the mobile communication device, a personal computer, a remote server, a cloud-based computing system, a computing module of any other suitable computing device (e.g., mobile computing device, wearable computing device, etc.), and any other suitable computing module. In transmitting the log of use dataset, a communication module (e.g., a hardware communication module associated with the communication application) can transmit data to the computing system by way of a wired and/or wireless data link (e.g., over Bluetooth, over Bluetooth LTE, etc.). However, Block S110 can include another other suitable variation of accessing the log of communication, transmitting data from the log of communication, and/or receiving a log of use dataset.

Block S120 recites: receiving a supplementary dataset characterizing mobility-behavior of the patient in association with the time period, which functions to unobtrusively receive non-communication-related data from a patient's mobile communication device and/or other device configured to receive contextual data from the patient. Block S120 can include receiving non-communication-related data pertaining to the patient before, during, and/or after (or in the absence of) communication with another individual (e.g., a phone call) and/or computer network (e.g., a social networking application), as described above in relation to Block S110. Block S120 can include receiving one or more of: location information, movement information (e.g., related to physical isolation, related to lethargy), device usage information (e.g., screen usage information related to disturbed sleep, restlessness, and/or interest in mobile device activities), and any other suitable information. In variations, Block S120 can include receiving location information of the patient by way of one or more of: receiving a GPS location of the individual (e.g., from a GPS sensor within the mobile communication device of the patient), estimating the location of the patient through triangulation (e.g., triangulation of local cellular towers in communication with the mobile communication device), identifying a geo-located local Wi-Fi hotspot during a phone call, and in any other suitable manner. In applications, data received in Block S110 and S120 can be processed to track behavior characteristics of the patient, such as mobility, periods of isolation, quality of life (e.g., work-life balance based on time spent at specific locations), and any other location-derived behavior information.

As such, data from Blocks S110 and S120 can thus be processed separately and/or can be merged in subsequent blocks of the method 100 to track the patient's mobility during a communication, for instance, in the analysis of Block S140. In variations, Block S120 can additionally or alternatively include receiving mobile usage data, including data indicative of screen unlocks and mobile application usage (e.g., by retrieving usage information from mobile operating system logs, by retrieving usage information from a task manager on a mobile communication device, etc.). Blocks S120 and/or S110 can therefore facilitate tracking of variations and periods of activity/inactivity for a patient through automatically collected data (e.g., from the patient's mobile communication device), in order to enable identification of periods of activity and inactivity by the patient (e.g., extended periods when the individual was hyperactive on the device or not asleep).

In additional variations, Block S120 can additionally or alternatively include receiving one or more of: physical activity- or physical action-related data (e.g., accelerometer data, gyroscope data, data from an M7 or M8 chip) of the patient, local environmental data (e.g., climate data, temperature data, light parameter data, etc.), nutrition or diet-related data (e.g., data from food establishment check-ins, data from spectrophotometric analysis, etc.) of the patient, biometric data (e.g., data recorded through sensors within the patient's mobile communication device, data recorded through a wearable or other peripheral device in communication with the patient's mobile communication device) of the patient, and any other suitable data. In examples, one or more of: a blood pressure sensor, and a pulse-oximeter sensor, and an activity tracker can transmit the individual's blood pressure, blood oxygen level, and exercise behavior to a mobile communication device of the individual and/or a processing subsystem implementing portions of the method 100, and Block S120 can include receiving this data to further augment analyses performed in Block S140.

In relation to receiving data, Blocks S120 and/or S110 can additionally or alternatively include receiving data pertaining to individuals in contact with the patient during the period of time, such that data from the individual who experiences states of psychosis and data from others in communication with the patient are received (e.g., using information from an analogous application executing on the electronic device(s) of others in communication with the individual). As such, Blocks S120 and/or S110 can provide a holistic view that aggregates communication behavior data and contextual data of two sides of a communication involving the patient who experiences states of psychosis. In examples, such data can include one or more of: a second party's location during a phone call with the patient, the second party's phone number, the second party's length of acquaintance with the patient, and the second party's relationship to the patient (e.g., top contact, spouse, family member, friend, coworker, business associate, etc.).

Similar to Block S110, In relation to receiving the supplementary dataset, Block S120 can include transmitting the supplementary dataset from the mobile communication device S122 and/or any other suitable device or system that serves as a source of supplementary data, to the computing system, as shown in FIG. 2. In transmitting the supplementary dataset, one or more sensor modules (e.g., sensor module of the mobile communication device, sensor module of a wearable computing device, sensor of a biometric monitoring device, etc.) can transmit data to the computing system by way of a wired and/or wireless data link (e.g., over Bluetooth, over Bluetooth LTE, etc.). However, Block S120 can include any other suitable variation of transmitting supplementary data, and/or receiving supplementary data.

1.2 Method—Active Data

Block S125 recites: receiving a survey dataset including responses, to at least one of a set of psychosis-assessment surveys, associated with a set of time points of the time period, from the patient. Block S125 thus functions to receive active data provided by surveying the patient, which can enable determination of a state of psychosis of the patient. Block S125 is preferably implemented at a module of the computing system described in relation to Block S110 above, but can additionally or alternatively be implemented at any other suitable system configured to receive survey data from one or more patients. The survey dataset can include interview and/or self-reported information from the patient. Furthermore, the survey dataset preferably includes quantitative data, but can additionally or alternatively include qualitative data pertaining to a psychotic state of the patient corresponding to at least a subset of the set of time points. Furthermore, while portions of the survey dataset preferably correspond to time points within the time period of Block S110, portions of the survey dataset can alternatively correspond to time points outside of the time period of Block S110 (e.g., as in a pre-screening or a post-screening survey). Additionally or alternatively, Block S125 can include receiving clinical data (e.g., information gathered in a clinic or laboratory setting by a clinician).

In Block S125, the set of time points can include uniformly or non-uniformly-spaced time points, and can be constrained within or extend beyond the time period of the log of use of the native communication application of Block S110. As such, in variations, the set of time points can include regularly-spaced time points (e.g., time points spaced apart by an hour, by a day, by a week, by a month, etc.) with a suitable resolution for enabling detection of changes in a psychotic state of the patient. Additionally or alternatively, provision of a survey and/or reception of responses to a survey can be triggered upon detection of an event of the patient (e.g., based upon data from sensors associated with the patient, based upon an output of an analysis of Block S140, etc.) or any other suitable change in psychosis state of the patient. Furthermore, for all time points of the set of time points, an identical subset of the set of psychosis-assessment surveys can be provided to the patient; however, in alternative variations, different subsets of the set of psychosis-assessment surveys can be provided to the patient at different time points of the set of time points.

In variations, the survey dataset can include responses to surveys configured to assess severity of psychosis (e.g., along a schizophrenia spectrum) in a patient along a spectrum, wherein the surveys transform qualitative information capturing a patient's affective state into quantitative data according to a response-scoring algorithm. In examples, the set of psychosis-assessment surveys can include surveys derived from one or more of: the Brief Psychiatric Rating Scale (i.e., a 16-18 item survey of psychiatric symptom constructs including somatic concern, anxiety, emotional withdrawal, conceptual disorganization, guilt feelings, tension, mannerisms and posturing, grandiosity, depressive mood, hostility, suspiciousness, hallucinatory behavior, motor retardation, uncooperativeness, unusual thought content, blunted affect, excitement, and disorientation, first published in 1962), with scores ranking from 0 (not assessed) to 7 (most severe) for each item; a Clinical Global Impression (CGI) rating scale (e.g., A CGI-S severity scale for mental disorders, a CGI-I improvement scale for mental disorders, a CGI therapeutic effect scale for mental disorders) configured to assess psychosis symptom severity along a scale of 1 (normal) to 7 (most severe), configured to assess psychosis symptom improvement along a scale of 1 (most improved) to 7 (most severe degradation in state), and/or configured to assess psychosis therapeutic effect along a 4×4 scale from 1 (unchanged to worse effect) to 2 (minimal effect) to 3 (moderate effect) to 4 (effect marked by side effects) rated as none to significantly interferes with patient's functioning; a Dimensions of Psychosis Symptom Severity scale provided by the American Psychiatric Association, with scores ranging from 0 (not present) to 4 (present and severe) for a set of symptoms (e.g., hallucinations, delusions, disorganized speech, abnormal psychomotor behavior, negative symptoms related to emotional expression, impaired cognition, depression, and mania); a Global Functioning Role (GFR) survey for phases of Schizophrenia; a Global Functioning Social (GFS) survey for phases of Schizophrenia; a Community Assessment of Psychic Experiences (CAPE) derived survey; a Scale for the Assessment of Positive Symptoms (SAPS) derived survey for delusional behavior, hallucinatory behavior, and/or disorganized speech behavior; and any other suitable tool or survey for assessment of psychosis.

Additionally or alternatively, other survey responses received in Block S125 can include one or more of: a demographic survey that receives demographic information of the patient; a medication adherence survey (for patients taking medication for a psychotic disorder); a mood survey; and a social contact survey (e.g., covering questions regarding aspects of the patient's contact with others). However, the set of surveys can include any other suitable surveys configured to assess mental states of the patient, or adaptations thereof. As such, the survey dataset can include quantitative scores of the patient for one or more subsets of surveys for each of the set of time points (or a subset of the set of time points).

In an example, the survey dataset comprises monthly responses to a GFS and a GFR survey, weekly responses (e.g., for a period of 5 months) to questions derived from the Brief Psychiatric Rating Scale (BPRS) survey, weekly responses (e.g., for a period of 5 months) to questions derived from a CGI survey (e.g., to assess symptoms of depression, anxiety, confusion, suspiciousness, anhedonia, avolition, auditory sensation, visual sensation, sleep, etc.), daily responses to a mood survey (e.g., a survey that prompts the user to provide an indication of mood on a scale from unhappy to happy), daily responses to a social contact survey (e.g., a survey that asks the user if face-to-face social contact occurred, a survey that asks the user if any social conflicts occurred), and twice-per-week responses to a medication adherence survey.

In some variations, Block S125 can further include facilitating automatic provision of at least one of the set of psychosis-assessment surveys at the mobile computing device(s) of the patient(s). As such, responses to one or more of the set of psychosis-assessment surveys can be provided by user input at an electronic device (e.g., a mobile computing device of the patient), or automatically detected from user activity (e.g., using suitable sensors). Additionally or alternatively, provision of at least one of the set of psychosis-assessment surveys can be performed manually by an entity associated with a patient or received as derived from clinical data, with data generated from the survey(s) received in Block S120 by manual input. Additionally or alternatively, provision of at least one survey and/or reception of responses to the survey can be guided by way of an application executing at a device (e.g., mobile device, tablet) of a caretaker of the patient and/or the patient, wherein the application provides instruction (e.g., in an audio format, in a graphic format, in a text-based format, etc.) for providing the survey or the responses to the survey. Block S125 can, however, be implemented in any other suitable manner (e.g., by verbal communication over the phone, by verbal communication face-to-face, etc.).

Similar to Block S110, In relation to receiving the survey dataset, Block S125 can include transmitting the survey dataset from the mobile communication device S126 and/or any other suitable device or system that serves as a source of survey data, to the computing system, as shown in FIG. 2. In transmitting the survey dataset, one or more data storage modules (e.g., memory module of the mobile communication device, etc.) can transmit data to the computing system by way of a wired and/or wireless data link (e.g., over Bluetooth, over Bluetooth LTE, etc.). However, Block S130 can include another other suitable variation of transmitting survey data, and/or receiving survey data.

Blocks S110, S120, and S125 can thus provide passive data (e.g., unobtrusively collected data) and active data (e.g., survey data) that can be taken as inputs in Block S130 to generate analyses pertaining to present, past, and/or future psychotic states of a patient.

Some variations of the method 100 can, however, omit collection of a survey dataset, such that analyses generated in subsequent blocks of the method 100 rely upon the log of use dataset and/or the supplementary dataset in enabling determination of a state of a psychosis of the patient. Thus, analyses of the state(s) of psychosis of the patient and/or predictive models generated in subsequent blocks of the method 100 can omit use of active data in determining states of the patient and providing appropriate therapies to the patient. Alternatively, variations of the method 100 can omit collection of one or more of the log of use dataset and the supplementary dataset, such that analyses generated in subsequent blocks of the method 100 rely upon the survey dataset in enabling determination of a state of a psychosis of the patient. Thus, analysis of the state(s) of psychosis of the patient and/or predictive models generated in subsequent blocks of the method 100 can omit use of portions of the datasets described in Blocks S110, S120, and S125 in determining states of the patient and providing appropriate therapies to the patient. Variations of the method 100 can additionally or alternatively include omission or collection of any other suitable type of data for use in subsequent blocks of the method 100.

1.3 Method—Modeling and Predicting Psychosis State

Block S130 recites: transforming data derived from at least one the log of use dataset, the supplementary dataset, and the survey dataset into an analysis of a psychotic episode-risk state associated with at least a portion of the time period. Block S130 functions to determine values of one or more psychotic episode-risk parameters in association with at least one time point of the set of time points, based upon one or more of the log of use dataset, the supplementary dataset, and the survey dataset. Block S130 thus enables assessment of a past or current state of psychosis of the patient and/or predicts risk that the patient will trend toward a different (e.g., worsened, improved, etc.) state of psychosis at a future time point.

In the analysis, Block S130 can identify parameters/triggering events directly from passive data (i.e., the log of use dataset, the supplementary dataset) and/or from active data (i.e., the survey dataset), or can additionally or alternatively implement a predictive model that processes either or both passive and active components to predict one or more present or future depressive states of the individual, with training data. Additionally or alternatively, for patients following a medication regimen for treatment or maintenance of health in relation to depression, the analyses of Block S130 can include generation of an adherence model that assesses or predicts adherence of the patient to the medication regimen as an output of the analysis.

1.3.1 Psychotic Episode-Risk State—Predictive Model

Preferably, generating a predictive model S140 in association with Block S130 includes utilization of one or more machine learning techniques and training data (e.g., from the patient, from a population of patients), data mining, and/or statistical approaches to generate more accurate models pertaining to the patient's states of psychosis (e.g., over time, with aggregation of more data). As such, Block S130 is preferably implemented at a computing system configured to process data from one or more of the log of use dataset, the supplementary dataset, and the survey dataset. The computing system can be the same computing system associated with one or more of Blocks S110-S130 of the method 100, or can alternatively be any other suitable computing system.

In generating the predictive model, Block S140 preferably uses input data including one or more of: communication behavior data from the log of use dataset, data from supplementary dataset, and data from the survey dataset to provide a set of feature vectors corresponding to time points of the time period. Feature selection approaches can include one or more of: factor analysis approaches that implement statistical methods to describe variability among observed features in terms of unobserved factors, in order to determine which features explain a high percentage of variation in data; correlation feature selection (CFS) methods, consistency methods, relief methods, information gain methods, symmetrical uncertainty methods, and any other suitable methods of feature selection. In variations, feature selection approaches can be implemented for any passive data (e.g., communication data, mobility-related data, activity-related data, biometric parameter-related data, etc.), wherein a linking analysis of Block S130 is then used to determine associations between features of passive data and states of a psychosis-related disorder determined from active data (e.g., of the survey dataset). Analysis of the passive data in relation to the active data, with regard to feature selection and associations between passive and active data can, however, be performed in any other suitable manner.

In one variation, the feature vectors can include features related to aggregate communication behavior, interaction diversity, mobility behavior (e.g., mobility radius as a measure of distance traveled by the patient within a given time period, such as the weekend), a number of missed calls, and a duration of time spent in a certain location (e.g., at home). In examples, feature vectors can be generated based upon aggregation of phone, text message, email, social networking, and/or other patient communication data for a particular period of time into one or more features for the patient for the particular time period. Furthermore, a feature can be specific to a day, a week, a month, a day period (e.g., morning, afternoon, evening, night), a time block during a day (e.g., one hour), a specific communication action (e.g., a single phone call, a set of communication actions of the same type (e.g., a set of phone calls within a two-hour period), all communications within a period of time, etc.). Additionally, combinations of features can be used in a feature vector. For example, one feature can include a weighted composite of the frequency, duration (i.e., length), timing (i.e., start and/or termination), and contact diversity of all outgoing voice (e.g., phone call) communications and a frequency, length, and timing and/or response time to (i.e., time to accept) incoming voice communications within the first period of time through a phone call application executing on the patient's mobile computing device. Feature vectors can additionally or alternatively include features based on analysis of voice communications, textual communications, mobile application activity usage, location data, and any other suitable data which can be based on variance, entropy, or other mathematical and probabilistic computations of basic data (e.g., a composite activity score, a composite socialization score, a work-life balance score, a quality-of-life score). However, the feature vectors can be determined in any other suitable manner.

In some variations, Block S140 can additionally or alternatively include deriving features based upon one or more of: audio data and visual data of the patient (e.g., during communication, at one or more time points of the set of time points), in order to include additional inputs into a risk model for determination of a psychotic-episode-risk parameter. In one variation, processing of audio data from the patient can be used to aspects of the voice and/or mood of a patient, in order generate feature vectors, incorporating voice-related parameters (e.g., pitch, volume, speed of speech, modulation of speech, differences in voice-related parameters for different contacts, etc.) that can be used to detect changes in the mental state of a patient that are indicative of entrance of a certain psychotic state. Additionally or alternatively, processing of visual data (e.g., images, video) of the patient can be used to aspects of the facial expressions, body language, and/or mood of a patient, in order generate feature vectors, incorporating facial expression- and/or body language-related parameters (e.g., eyebrow position, pupil dilation, expressions indicative of positive mood, expressions indicative of negative mood, stance, speed of movement, etc.) that can be used to detect changes in the mental state of a patient that are indicative of entrance of a certain state of psychosis. As such, feature vectors processed by a predictive model in Block S140 can include elements derived from audio and/or visual data, in order to characterize or anticipate changes in a patient's state of psychosis. In specific examples, such features can even be used to classify or diagnose patients with specific types of psychotic or mental disorders, including disorders along a schizophrenia spectrum, along a bipolar-disorder spectrum, and/or any other suitable disorder (e.g., a disorder described in a Diagnostic and Statistical Manual of Mental Disorders).

In some variations, Block S140 can include utilizing statistics-based feature selection approaches to determine a subset of features from the log of use dataset, the supplementary dataset, and/or the survey dataset that have a high predictive power and/or high accuracy in generating one or more outputs of the predictive model. In examples, the statistical approaches can implement one or more of: correlation-based feature selection (CFS), minimum redundancy maximum relevance (mRMR), Relief-F, symmetrical uncertainty, information gain, decision tree analysis (alternating decision tree analysis, best-first decision tree analysis, decision stump tree analysis, functional tree analysis, C4.5 decision tree analysis, repeated incremental pruning analysis, logistic alternating decision tree analysis, logistic model tree analysis, nearest neighbor generalized exemplar analysis, association analysis, divide-and-conquer analysis, random tree analysis, decision-regression tree analysis with reduced error pruning, ripple down rule analysis, classification and regression tree analysis) to reduce questions from provided surveys to a subset of effective questions, and other statistical methods and statistic fitting techniques to select a subset of features having high efficacy from the data collected in Blocks S110, S120, and/or S125. Additionally or alternatively, any assessment of redundancy or efficacy in a feature derived from data of Blocks S110, S120, and/or S125 can be used to provide a measure of confidence in an output of the predictive model from one or more input features. Furthermore, the statistical approach(es) of Block S140 can be used to strategically reduce portions of data collected based upon redundancy and/or lack of utility of the data. Even further, the statistical approaches/feature selection approaches can be used to entirely omit collection of portions of the data (e.g., responses to specific surveys or portions of surveys can render responses to other portions of surveys or other surveys redundant), in order to streamline the data collection in Blocks S110, S120, and/or S125.

In one example, a high degree of correlation (e.g., positive correlation) between responses to a BPRS-derived survey and a daily mood survey (e.g., a portion of recent responses to a daily mood survey in relation to a time point of interest, responses to the daily mood survey in proximity to responses to a BPRS-derived survey) can be used to entirely omit provision of the BPRS-derived survey or portions of the BPRS-derived survey, in lieu of the daily mood survey, due to redundancy in data collection, in variations of the method 100. In more detail, high degrees of correlation between 1) BPRS positive symptoms and self-reported suspiciousness; 2) BPRS depression/anxiety and self-reported anxiety; 3) BPRS depression/anxiety and self-reported avolition/amotivation; and 4) BPRS depression/anxiety and self-reported sadness/depression can be used to omit provision of the BPRS-derived survey or portions of the BPRS-derived survey, and/or portions of surveys that prompt self-reported symptoms.

In another example associations 1) BPRS depression/anxiety and amount of sleep, and/or 2) between BPRS mania and amount of sleep, wherein sleep is self-reported by the patient or determined from a device (e.g., wearable computing device, bed-coupled device) configured to provide sleep data, can be used to omit provision of the BPRS-derived survey or portions of the BPRS-derived survey.

In another example, a high degree of correlation (e.g., positive correlation) between responses to a GFR, GFS, and/or CGI-derived survey and a social contact survey and mobile device usage behavior (e.g., screen unlock data) can be used to entirely omit provision of the GFR, GFS, and/or CGI-derived survey, in lieu of the social contact survey and mobile usage behavior, due to redundancy in data collection, in variations of the method 100. In still another example, a high degree of correlation (e.g., positive correlation) between a communication parameter derived from the log of use (e.g., call count predictability) and mobility data from the supplementary dataset can be used to entirely omit collection of data (e.g., call count data, mobility data) due to redundancy in data collection, in variations of the method 100. In still another example, a high degree of correlation (e.g., positive correlation) between responses to the mood survey and sleep behavior (e.g., as indicated from usage and/or unlocking of a mobile device) from the supplementary dataset can be used to entirely omit collection of data (e.g., mood survey responses) due to redundancy in data collection, in variations of the method 100. As such, risk of entering a certain psychotic state can, with sufficient data and training of a risk model) be determined based solely upon passive data collect from the patient's interactions with his/her device(s).

In still other examples, correlations between active data and passive data can be used to streamline data collection associated with Blocks S110, S120, and/or S125. However, any other suitable data derived from Blocks S110, S120, and S125 can be used to increase efficacy of data collection and/or determination of values of the psychotic-episode-risk parameter in Blocks S130 and S140. Additionally or alternatively, any assessment of redundancy or efficacy in a feature derived from data of Blocks S110, S120, and/or S125 can be used to provide a measure of confidence in a psychotic-episode-risk parameter determined from the feature(s).

In some embodiments, the predictive model generated in Block S140 can process a set of feature vectors according to methods described in relation to the predictive modeling engine described in U.S. application Ser. No. 13/969,339, entitled "Method for Modeling Behavior and Health Changes" and filed on 16 Aug. 2014, which is incorporated herein in its entirety by this reference; however, the predictive model can alternatively be generated in any other suitable manner. As such, in variations of the model(s), a set of feature vectors from the input data can be processed according to a machine learning technique (e.g., support vector machine with a training dataset) to generate the value(s) of the criticality parameter in association with a time point. In one example, the predictive model can incorporate historical data from the patient (e.g., survey responses from a prior week, a history of passive data from the log of use, etc.), with more weight placed upon more recent data from Blocks S110-S125 in determination of a psychotic episode-risk state associated with a time point by the predictive model; however, the predictive model can be implemented in any other suitable manner.

Furthermore, in extensions of the method 100 to a population of patients, the predictive model can be used to identify differences in passive data and/or active data, as associated with identified depression-risk states, between different demographics of individuals. For instance, the predictive model can be used to identify sets of feature vectors and/or subsets of features (e.g., related to communication behavior, related to survey responses, related to mobility behavior, etc.) that have high efficacy in determining risk/severity for one or more of: different genders, different age groups, different employment statuses, different ethnicities, different nationalities, different socioeconomic classes, and any other suitable demographic difference.

While some variations of machine learning techniques are described above, in relation to generation of the predictive model, Block S140 can additionally or alternatively utilize any other suitable machine learning algorithms. In variations, the machine learning algorithm(s) can be characterized by a learning style including any one or more of: supervised learning (e.g., using logistic regression, using back propagation neural networks), unsupervised learning (e.g., using an Apriori algorithm, using K-means clustering), semi-supervised learning, reinforcement learning (e.g., using a Q-learning algorithm, using temporal difference learning), and any other suitable learning style. Furthermore, the machine learning algorithm can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked auto-encoder method, etc.), a dimensionality reduction method (e.g., principal component analysis, partial lest squares regression, Sammon mapping, multidimensional scaling, projection pursuit, etc.), an ensemble method (e.g., boosting, boostrapped aggregation, AdaBoost, stacked generalization, gradient boosting machine method, random forest method, etc.), and any suitable form of machine learning algorithm.

1.3.2 Psychotic Episode-Risk State—Adherence Model

For patients taking medication to manage their depression, Block S140 can additionally or alternatively include processing datasets associated with Blocks S110, S120, and/or S125 with an adherence model S145 configured to assess and/or predict a state of adherence to a medication regimen by a patient. The adherence model can be an embodiment, variation, or example of an adherence model as described in U.S. application Ser. No. 13/969,339, entitled "Method for Modeling behavior and Health Changes", but can alternatively be any other suitable adherence model.

Figure 3:
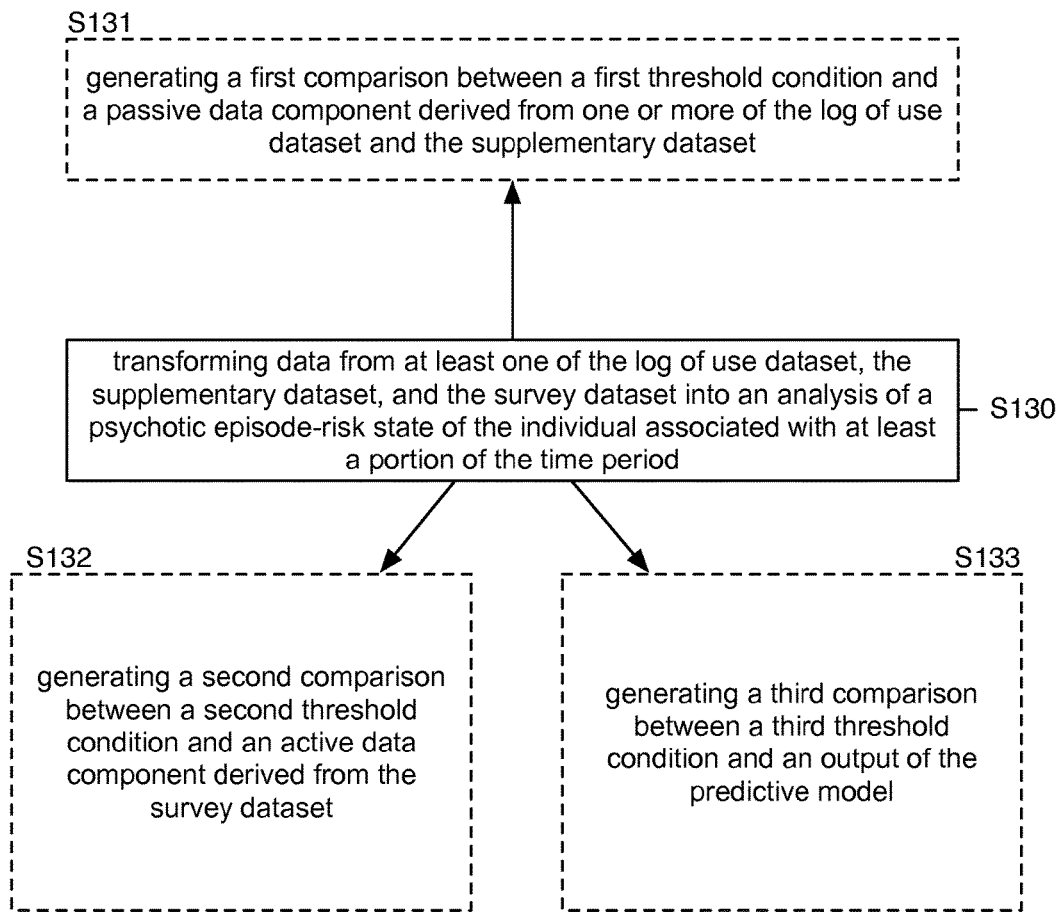
FIG. 3 depicts a flowchart of a portion of an embodiment of a method for modeling behavior and psychosis.

1.3.3 Psychotic Episode-Risk State—Parameters of Analysis and Criticality Assessment In generating the analysis of a psychotic episode-risk state of the individual, Block S130 can include generating comparisons between different threshold conditions and one or more of: components of the log of use dataset, components of the supplementary dataset, components of the survey dataset and outputs of the predictive model. As such, generating the analysis of the psychotic episode-risk state of the individual in Block S130 can include one or more of: generating a first comparison between a first threshold condition and a passive data component derived from one or more of the log of use dataset and the supplementary dataset S131; generating a second comparison between a second threshold condition and an active data component derived from the survey dataset S132; and generating a third comparison between a third threshold condition and an output of the predictive model S133, as shown in FIG. 3. The comparison(s) generated in Blocks S131-S133 can thus indicate that the value(s) of parameters associated with states of psychosis (e.g., critical states of psychosis) is/are one or: above the associated threshold condition(s), not significantly different from the associated threshold condition(s), and below the associated threshold condition(s) in triggering the alert of Block S140, wherein, in a specific example, alerts are triggered if the value(s) of parameters associated with a critical state of psychosis is/are above the associated threshold condition(s). Even further, the comparison(s) to the threshold condition(s) can be based upon multiple values of a parameter or different parameters (e.g., parameters of active data, parameters of passive data, parameters from a predictive model, etc.) in combination. In Blocks S131-S133, the threshold condition(s) can be a threshold value of a parameter or a threshold range of values, wherein the threshold range of values is defined by a first limiting value and a second limiting value. Comparison to the threshold condition(s) in Blocks S131-S133 can thus be performed in a manner that is inclusive of a limiting value, or alternatively be performed in a manner that is exclusive of a limiting value.

Figure 4:
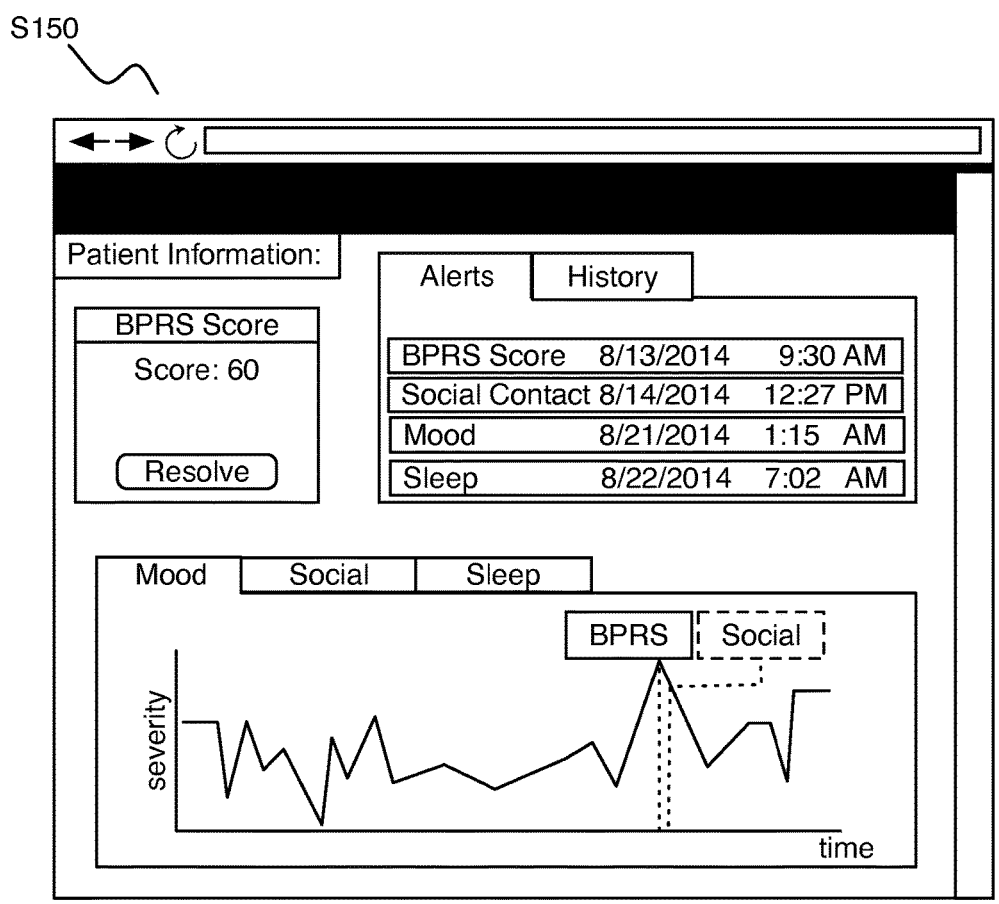
FIG. 4 depicts an example of a dashboard for providing an alert in an embodiment of a method for modeling behavior and psychosis.

The comparisons of Blocks S131, S132, and/or S133 can thus be associated with parameters of the psychotic episode-risk state of the individual used to assess criticality of the state of psychosis of the patient, and/or to resolve a critical state of psychosis of the patient in subsequent blocks of the method 100. Blocks S131, S132, and S133 thus function to process the outputs of Blocks S110, S120, and S140 of the method 100, such that the resolution actions of Block S150 are derived from at least one of an active component (i.e., a component derived from the survey response dataset), a passive component (e.g., a clinically-informed behavioral rule component determined by heuristics), and a component derived from the predictive model generated in Block S142. In particular, consideration of the active component, the passive component, and the component derived from the predictive model can significantly strengthen the efficacy of the resolution actions implemented in Block S150, as shown in FIG. 4. Furthermore, each of the active component, the passive component, and the predictive model component can have an associated time frame that is identical or different to time frames of analysis of the other components. Additionally, analysis of each of the active component, the passive component, and the predictive model component can occur within one or more time frames that are different from the time frame of an associated resolution action.

Block S131 recites: generating a first comparison between a first threshold condition and a passive data component derived from one or more of the log of use dataset and the supplementary dataset. In Block S131, generating the comparison between the first threshold condition and a passive data element can comprise defining one or more categories of passive behaviors of the individual (e.g., related to lethargy, related to social isolation, related to physical isolation, related to evolution of the patient's support network, related to time spent at work, related to weekly behavioral patterns, etc.) based upon historical behavior of a patient within a duration of time (e.g., immediately prior 4-6 weeks of the individual's life). Then, Block S131 can include comparing the features of, or evolution in the passive behavior(s) of, the individual to the first threshold condition. In variations wherein the passive behaviors of the patient are monitored for a duration of time, the first threshold condition can additionally or alternatively include a frequency threshold and/or a frequency-within-a-duration-of-time threshold, in relation to generation of an indication based upon a passive data component.

In variations, the first threshold condition can include one or more of: a threshold condition of a mobility-related parameter than the $10^{th}$ percentile of values of the mobility-related parameter (e.g., mobility radius) for the time period (e.g., a time window of 30 days, including 15 values of the mobility-related parameter) for the patient; a threshold condition of a mobility less than the $20^{th}$ percentile of values of a mobility-related parameter (e.g., mobility radius) for the time period (e.g., a time window of 30 days, including 15 values of the mobility-related parameter); a threshold condition of a number of outgoing SMS messages less than 2 messages per day for a period of three consecutive days (e.g., which is correlated with higher BPRS positive symptom scores and higher BPRS depressive symptom scores); a threshold condition of a number of incoming SMS messages less than 2 messages per day for a period of 5 consecutive days; any other suitable threshold condition; and any other suitable combination of threshold conditions.

In examples, the first comparison can thus facilitate identification of one or more of: a period of social isolation exhibited as persistence in reduced outgoing communications and/or reduced incoming communications (e.g., a period of 2 days of unreturned phone calls, a period of 2 days of unreturned text-based communications, etc.); a period of physical isolation exhibited as persistence in staying in a location (e.g., staying primarily at the same location for a period of 3 or more days); a reduction in the individual's support network exhibited as communicating with fewer people than typical for the patient; a period of lethargy exhibited as a persistent reduction in mobility (e.g., little motion over a period of 3 consecutive days); a combination of multiple passive behaviors that satisfy a threshold condition (e.g., two passive behaviors that meet a threshold within 3 days); and any other suitable condition for indication generation.

Block S132 recites: generating a second comparison between a second threshold condition and an active data component derived from the survey dataset. In Block S132, generating the second comparison between the second threshold condition and the active component derived from the survey response dataset can comprise assigning a score to one or more elements of the survey response dataset for a patient (e.g., based upon one instance of survey response provision, based upon multiple instances of survey response provision), and comparing the score(s) to the second threshold condition. In variations wherein the survey response dataset comprises responses to survey questions (e.g., a repeat set of survey questions) at each of a set of time points, the second threshold condition can additionally or alternatively include a frequency threshold and/or a frequency-within-a-duration-of-time threshold, in relation to generation of an indication based upon an active component. Furthermore, threshold conditions can be defined in relation to a baseline for each patient, as determined from historical behavior of the patient.

As such, in variations, the second comparison can indicate one or more of: a score greater than a given threshold; a score greater than a given threshold for a certain duration of time; a change in score greater than a given threshold; a change in score greater than a given threshold as derived from the patient's historical score data; and any other suitable comparison. Furthermore, the comparison(s) can additionally or alternatively be generated based upon a percentile condition, a standard deviation (e.g., in score) condition, outlier detection analysis (e.g., of a score in relation to scores from the individual), and/or any other suitable condition, based upon analysis of a patient in isolation, based upon analysis of the individual's recent behavior in isolation, based upon analysis of a population of patients, and/or any other suitable grouping of patients.

In examples, the second comparison can comprise a comparison to one or more of: a threshold condition of three (e.g., consecutive, non-consecutive) BPRS derived survey scores greater than or equal to 70, with a difference greater than 20; a threshold condition of one BPRS survey score greater than 90; a threshold condition of a score greater than 0 on a portion of a psychosis-assessment survey related to self or outwardly afflicted harm; a threshold condition of scores fluctuating significantly across three consecutive days on a mood survey; a threshold condition pertaining to a period of time (e.g., 1 day, 3 days) for a lapse in adherence to a medication regimen; and a threshold condition of scores fluctuating significantly across five consecutive days on a social contact survey (e.g., in relation to face-to-face social contact, in relation to number of conflicts).

Block S133 recites: generating a third comparison between a third threshold condition and an output of the predictive model. In Block S133, generating the third comparison between the third threshold condition and the output of the predictive model can comprise identification of a classification (e.g., a learned, complex, non-intuitive, and/or behavioral association exhibited by the individual), and comparing the classification to a threshold condition. In variations, a single feature and/or combinations of features derived from the log of use dataset, the supplementary dataset, and, the survey response dataset (e.g., with weighting among factors) can be compared to one or more threshold conditions, in identifying if an alert based upon the predictive model of Block S140 should be generated. In variations and examples, the third comparison can be generated as described in U.S. application Ser. No. 13/969,339, entitled "Method for Modeling Behavior and Health Changes" and filed on 16 Aug. 2014.

As such, in one example of Blocks S131, S132, and S133, accounting for a passive component, an active component, and a predictive model component, a determination of a state of psychosis of the patient can be based upon: a first passive component (e.g., related to communication behavior) generated from behavior analyzed over a first duration of time, a second passive behavioral component (e.g., related to mobility of the individual) generated from behavior analyzed over a second duration of time overlapping with the first duration of time, scoring of a biweekly survey, and a predictive model component for third duration of time (e.g., overlapping with the period of the biweekly survey), wherein the predictive model component implements an aggregated learning approach based upon multiple individual models (e.g., each assessing different parameters and/or different time periods of patient behavior).

The analyses of Block S130 can, however, include generation of any other suitable comparison and/or any other suitable output which serve as parameters of the psychotic episode-risk state of the individual. Additionally or alternatively, the comparison(s) generated in Blocks S131, S132, and S133 can include identification or analysis of patient progress through a condition (e.g., in relation to persistence of symptoms, in relation to worsening of symptoms, in relation to improvement of symptoms, etc.).

1.4 Method—Resolution of Critical States of Psychosis

Block S150 recites: generating an alert based upon one or more outputs of the analysis, which functions to provide an indication that the patient is experiencing a critical state of psychosis and/or is trending toward a critical state of psychosis. Block S150 can thus include generating an alert upon detection, at the computing system performing the analysis, that one or more outputs (e.g., comparisons) from the analysis of the psychotic episode-risk state satisfy associated threshold conditions. The alert of Block S150 can be an alert that prompts transmission of a notification to an entity associated with the patient, for instance, for therapeutic intervention. The alert can additionally or alternatively comprise an alert that serves as an input into a subsequent computer-implemented module for automatically providing an intervention to the patient, the intervention intended to improve the psychosis-related state of the patient.

As such, Block S150 can include Block S152, which recites: transmitting an alert based upon the analysis. Block S152 functions to alert at least one of: 1) an entity associated with the patient and 2) the patient regarding a critical value of one or more values of the psychotic-episode-risk parameters, or of a critical state of psychosis that the patient has or will enter. The alert can be a visual alert (e.g., text-based alert, graphic alert), audio alert, haptic alert, and/or any other suitable type of alert. In relation to an entity associated with the patient(s), the entity can include any one or more of: a caretaker, a healthcare provider, a relative (e.g., parent, significant other, etc.), and any other suitable entity associated with the patient. Furthermore, in relation to an entity associated with the patient(s), the alert(s) can be provided at a dashboard of an electronic interface (e.g., web portal, computing device, etc.) accessible by the entity. In the example shown in FIG. 4, alert(s) of Block S152 can be provided at a dashboard of a web portal, wherein the alert(s) are text-based alerts including a type of alert (e.g., related to active data, related to passive data), a value of a psychotic-episode-risk parameter associated with the alert, and a graphic that displays values of one or more scores of a survey (e.g., a daily mood survey) and/or a psychotic-episode-risk parameter over time. In the example, the graphic can include tags that facilitate identification of associations between metrics derived from active data and passive data (e.g., mobility parameter values in association with scores on a BPRS, GFR, GFS, or CGI derived survey, scores on a social contact survey, and/or scores on a daily mood survey). The dashboard can further provide an option to resolve the alert, wherein in examples, resolution of the alert can include any one or more of: triaging a patient's psychotic state, providing emotional support to the patient to improve the patient's psychotic state, assessing the level of follow up care needed to improve the patient's state (e.g., by facilitating an appointment with a primary care physician within 3 days, by alerting a friend of the patient, by facilitating immediate transfer of the patient to an emergency room, etc.), by providing a short term plan to the patient to improve the patient's psychotic state in an acute manner, by providing a long term plan to the patient that is configured to maintain a healthy state of the patient, and any other suitable resolving act (e.g., storing information/data resulting from a resolution action for future reference).

In relation to the comparison(s) of Blocks S131, S132, and S133, the alert can comprise an alert associated with passive data (e.g., alerts related to lethargy associated with a mobility parameter, alerts related to social isolation in association with unreturned calls, alerts related to physical isolation in association with time spent at a location alone, alerts associated with reaching out to a support network associated with number of communication counts, alerts associated with reaching out to a support network associated with communication diversity, etc.). Additionally or alternatively, the alert can comprise an alert associated with active data (e.g., alerts related to high BPRS scores, alerts related to alerts related to fluctuations in daily mood scores, alerts related to medication adherence, alerts related to poor social contact, etc.). However, in variations of the specific examples noted above, the alerts can be associated with any other suitable form of active/passive data derived from other blocks of the method 100. As such, the alert can comprise any other suitable alert configured to facilitate improvement of the psychotic state of the patient, including identification of factors or triggers (e.g., substance abuse, medication non-adherence, stressful life events, natural course of psychotic illness, etc.) contributing to lapses in the patient's psychotic state, in order to intervene at an acute phase of the patient's psychosis.

Figure 5A:
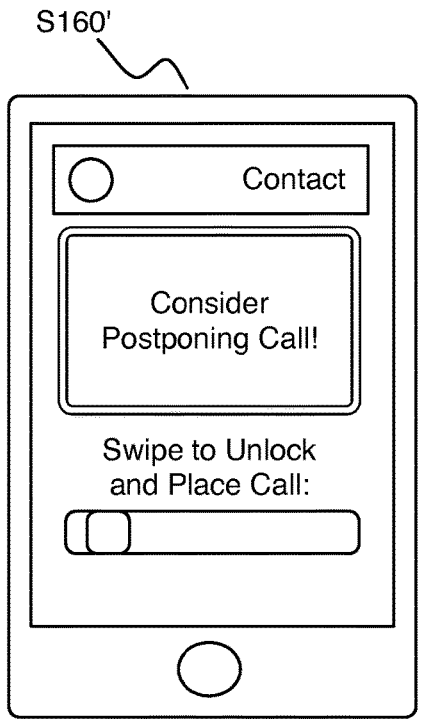
FIGS. 5A-5C depict example notifications in an example of a method for modeling behavior and psychosis.
Figure 5B:
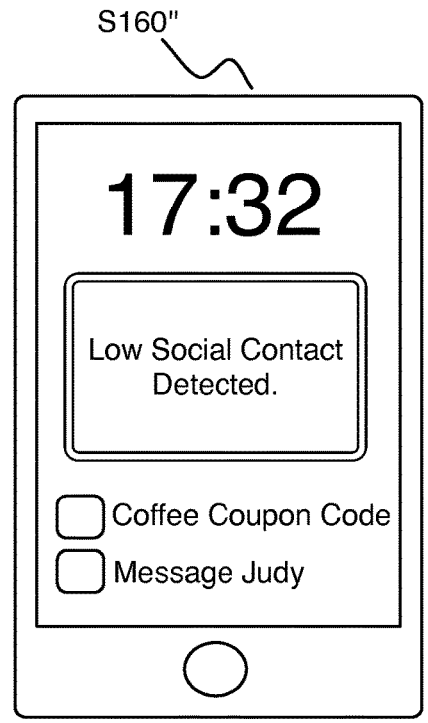
Figure 5C:

In some variations, the method 100 can further include Block S160, which recites: providing a notification to the patient, at the mobile communication device, in response to the analysis. Block S160 functions to provide information, advice, and/or motivational content to the patient so that the patient can improve his/her psychotic state, can avoid conflicts, can avoid situations that could worsen his/her psychotic state, and/or can maintain a healthy state. In variations of Block S160, the notifications can be provided with any suitable regular or non-regular frequency, can be provided with a sequence or in a random manner, can be triggered by an event, or can be provided in any other suitable manner. Furthermore, the notifications can include one or more of: a visual notification (e.g., text-based notification, graphic notification), an audio notification, a haptic notification, and any other suitable type of notification. In one example, a mobile computing device of a patient can download and subsequently display the notification for the patient at a display of the mobile computing device, as shown in FIGS. 5A-5C, where examples of notifications are depicted as S160', S160", and S160'". The notifications can be personalized to the patient, or can be provided in the same manner to each of a population of patients. In variations wherein the notifications are personalized to the patient, Block S160 can utilize a machine learning technique or any other suitable computational process, as described above, to identify the types of notifications that the patient responds positively to and/or negatively to, as assessed by patient outcomes in relation to psychotic state (e.g., indicated in values of the psychotic-episode-risk parameter).

In one example, the notification can provide advice to the patient, based upon the analysis, to avoid contact with people identified in Blocks S130 and S140 to produce degradation in the patient's psychotic state, based upon the analysis. In another example, the notification can provide advice to the patient, based upon the analysis, to avoid travel to certain locations identified in Blocks S130 and S140 to produce degradation in the patient's state of psychosis. In another example, the notification can notify the user of a period of lack of social contact, and can additionally or alternatively set reminders for the patient to contact entities identified to have a positive impact on the patient's state of psychosis. In another example, the notification can provide the user with incentives (e.g., coupons, discounts) to increase his/her mobility or social contact, thereby preventing degradation in the patient's state of psychosis. The notification can additionally or alternatively be provided as described in U.S. application Ser. No. 13/969,339, entitled "Method for Modeling Behavior and Health Changes", and/or in any other suitable manner.

In some variations, the method 100 can additionally or alternatively include Block S170, which recites: automatically initiating provision of a therapeutic intervention for the individual by way of at least one of the computing system and the mobile communication device. Block S170 functions to actively promote improvements to the patient's psychotic state, and/or to facilitate maintenance of a healthy state in the patient. In variations, the therapeutic intervention can include a therapy regimen that delivers therapeutic measures to the patient, as facilitated by at least one of the computing system and the mobile communication device. Generation and/or provision of the therapeutic intervention(s) can thus be facilitated through one or more of: an application executing on an electronic device (e.g., mobile device, tablet, personal computer, head-mounted wearable computing device, wrist-mounted wearable computing device, etc.) of the patient, a web application accessible through an internet browser, an entity (e.g., caretaker, spouse, healthcare provider, relative, acquaintance, etc.) trained to provide the therapy regimen, and in any other suitable manner. In examples, portions of a therapy regimen can be delivered in-app through the mobile communication device, and/or interactions between the patient and a therapeutic entity can be established using modules of the computing system.

In variations, the therapeutic measures provided in Block S170 can include any one or more of: psychiatric management measures (e.g., education of the patient, education of acquaintances of the patient, forming alliances, providing support groups, etc.), pharmacotherapeutic measures (e.g., antipsychotic medications, benzodiazepines, antidepressants, mood stabilizers, beta blockers), psychotherapeutic measures (e.g., cognitive behavioral therapy, interpersonal therapy, problem solving therapy, psychodynamic psychotherapy), psychosocial interventions, weight management interventions (e.g., to prevent adverse weight-related side effects due to medications) electroconvulsive therapeutic measures, and any other suitable therapeutic measure.

Furthermore, the therapy regimen and/or other therapeutic interventions can be provided using one or more of: healthcare provider interactions (e.g., therapeutic sessions with a counselor), pharmaceutical compound distributors, mobile application implemented methods, web browser-facilitated methods, and any other suitable avenue of therapy provision. The therapeutic interventions of Block S170 can additionally or alternatively be provided in a manner similar to that described in U.S. application Ser. No. 13/969,339, entitled "Method for Modeling Behavior and Health Changes", with therapy/treatment efficacy analyzed by a treatment regimen model and/or a treatment efficacy model. The therapy regimen can, however, be provided in any other suitable manner or assessed in any other suitable manner.

The method 100 can, however, include any other suitable blocks or steps configured to model behavior and psychotic state, and/or improve a psychotic state of a patient. Furthermore, as a person skilled in the art will recognize from the previous detailed description and from the figures and claims, modifications and changes can be made to the method 100 without departing from the scope of the method 100.

2. System

Figure 6:
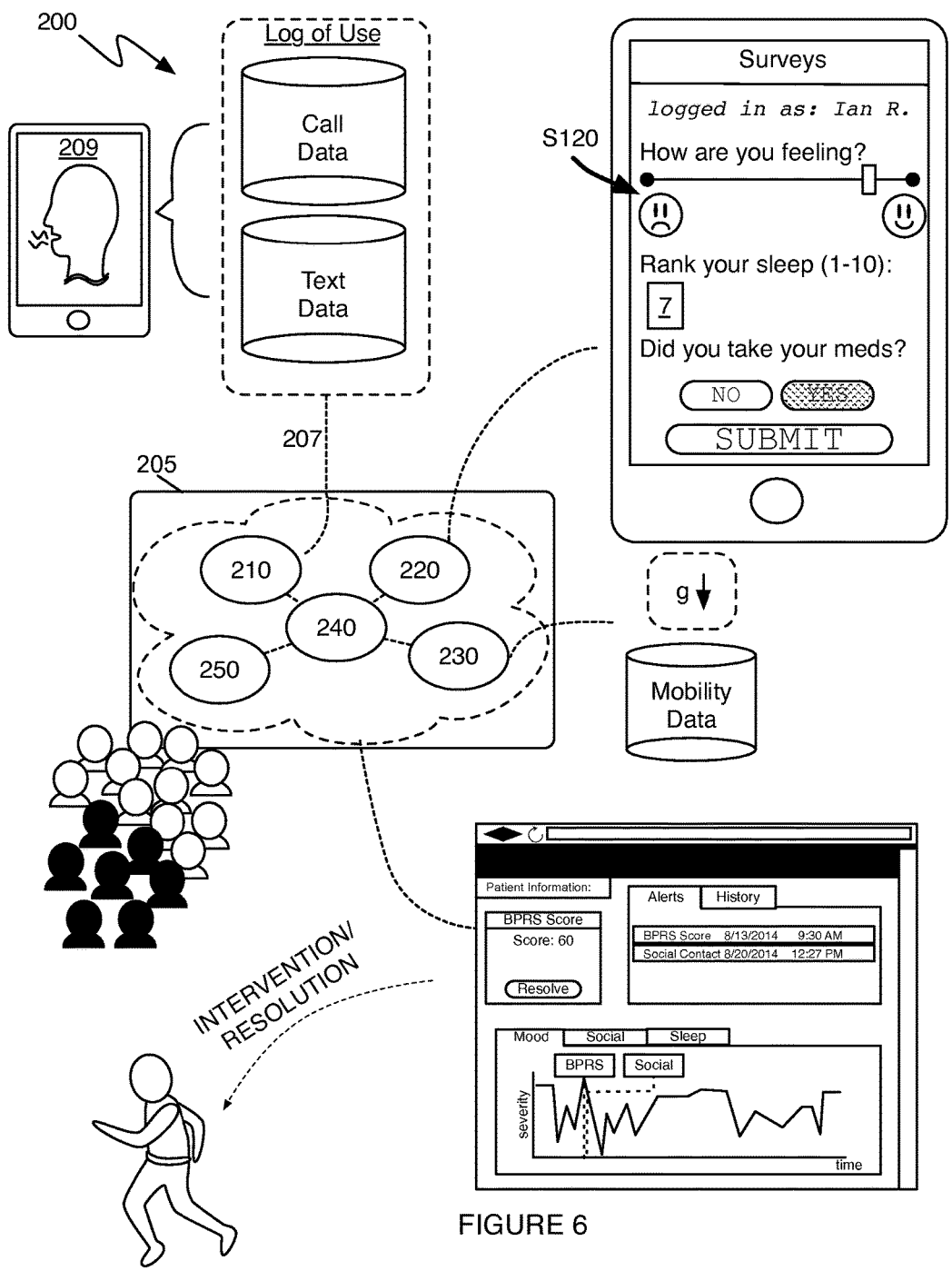
FIG. 6 depicts an embodiment of a system for modeling behavior and psychosis.

As shown in FIG. 6, a system 200 for modeling behavior and psychosis of a patient includes: a processing system 205 including: an interface 207 with a native data collection application executing on a mobile computing device 209 of the patient; a first module 210 configured to access a log of use of a native communication application coupled to the native data collection application on the mobile computing device by the patient within a time period; a second module 220 configured to receive a supplementary dataset characterizing activity of the patient in association with the time period; a third module 230 configured to receive a survey dataset including responses, to at least one of a set of psychosis-assessment surveys, associated with a set of time points of the time period, from the patient; a fourth module 240 configured to transform data from the log of use, the survey dataset, and the supplementary dataset into an analysis of a psychotic episode-risk state of the individual; and a fifth module 250 configured to generate an alert based upon one or more outputs of the analysis. The system 200 can incorporate, at least in part, embodiments, variations, and examples of elements of the system described in U.S. application Ser. No. 13/969,339 entitled "Method for Modeling Behavior and Health Changes" and filed on 16 Aug. 2013.

The system 200 functions to perform at least a portion of the method 100 described in Section 1 above, but can additionally or alternatively be configured to perform any other suitable method for modeling behavior and psychosis of a patient. The system 200 is preferably configured to facilitate reception and processing of a combination of active data (e.g., survey responses) and passive data (e.g., unobtrusively collected communication behavior data, mobility data, etc.), but can additionally or alternatively be configured to receive and/or process any other suitable type of data. As such, the processing system 205 can be implemented on one or more computing systems including one or more of: a cloud-based computing system (e.g., Amazon EC3), a mainframe computing system, a grid-computing system, and any other suitable computing system. Furthermore, reception of data by the processing system 205 can occur over a wired connection and/or wirelessly (e.g., over the Internet, directly from a natively application executing on an electronic device of the patient, indirectly from a remote database receiving data from a device of the patient, etc.).

The processing system 205 and data handling by the modules of the processing system 205 are preferably adherent to health-related privacy laws (e.g., HIPAA), and are preferably configured to privatize and/or or anonymize patient data according to encryption protocols. In an example, when a patient installs and/or authorizes collection and transmission of personal communication data by the system 200 through the native data collection application, the native application can prompt the patient to create a profile or account. In the example, the account can be stored locally on the patient's mobile computing device 209 and/or remotely. Furthermore, data processed or produced by modules of the system 200 can be configured to facilitate storage of data locally (e.g., on the patent's mobile computing device, in a remote database), or in any other suitable manner. For example, private health-related patient data can be stored temporarily on the patient's mobile computing device in a locked and encrypted file folder on integrated or removable memory. In this example, the patient's data can be encrypted and uploaded to the remote database once a secure Internet connection is established. However, patient data can be stored on any other local device or remote data in any other suitable way and transmitted between the two over any other connection via any other suitable communication and/or encryption protocol. As such, the modules of the system 200 can be configured to perform embodiments, variations, and examples of the method 100 described above, in a manner that adheres to privacy-related health regulations.

The method 100 and/or system 200 of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a patient computer or mobile device, or any suitable combination thereof. Other systems and methods of the embodiments can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor, though any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method for improving psychotic disorder-related state determination for a patient, the method comprising:
    transmitting, from a communication module executing on a mobile communication device to a computing system, a log of use dataset associated with communication behavior of the patient during a time period;
    at the computing system, receiving a motion supplementary dataset corresponding to a motion sensor of the mobile computing device, the motion supplementary dataset characterizing mobility-behavior of the patient during the time period;
    collecting GPS data corresponding to a GPS sensor of the mobile device, the GPS data associated with location behavior of the patient in association with the time period;
    selecting a patient subgroup for the patient from a first subgroup and a second subgroup based on the GPS data and the motion supplementary dataset, wherein the first subgroup is selected in response to the GPS data and the motion supplementary dataset indicating a first mobility behavior associated with the first subgroup, wherein the second subgroup is selected in response to the GPS data and the motion supplementary dataset indicating a second mobility behavior associated with the second subgroup, and wherein selection of the patient subgroup is operable to improve data storage, data retrieval, and the psychotic disorder-related state determination;
    at the computing system, generating a predictive model based upon the selected patient subgroup and a passive dataset derived from the log of use dataset and the motion supplementary dataset;
    transforming at least one of the passive dataset and an output of the predictive model into an analysis of a psychotic episode-risk state of the patient associated with at least a portion of the time period; and
    upon detection that parameters of the psychotic episode-risk state satisfy at least one threshold condition, automatically initiating provision of a therapeutic intervention for improving a health outcome of the patient, by way of at least one of the computing system and the mobile communication device.

2. The method of claim 1, further including: providing, by way of an application of the mobile communication device, at least one of a set of psychosis-assessment surveys to the patient; and at the computing system, receiving a survey dataset including responses, to at least one of the set of psychosis-assessment surveys, associated with a set of time points of the time period.

3. The method of claim 2, wherein providing at least one of a set of psychosis-assessment surveys includes automatically providing a first portion of a survey within the application at a first subset of time points of the time period, and providing a second portion of the survey within the application at a second subset of time points of the time period.

4. The method of claim 2, wherein the survey dataset includes responses to a Brief Psychiatric Rating Scale (BPRS)-derived survey, a mood information survey, and a sleep information survey, and wherein generating the predictive model comprises generating the predictive model from a) the survey dataset and b) the passive dataset.

5. The method of claim 4, wherein generating the analysis includes determining an amount of sleep per night of the patient over a portion of the time period from the sleep information survey, and generating an alert configured to initiate provision of the therapeutic intervention, upon detection that the amount of sleep is below a threshold amount and that responses to the BPRS-derived survey contribute to a BPRS score above a threshold score.

6. The method of claim 1, wherein transmitting the log of use dataset further includes: at the computing system, extracting, from the log of use dataset: a number of incoming text messages and a number of outgoing text messages.

7. The method of claim 6, wherein receiving the motion supplementary dataset includes extracting at least one of a location of the patient and mobility-related parameter associated with at least one time point of the time period and derived from the GPS sensor of the mobile communication device.

8. The method of claim 7, wherein generating the analysis includes generating a first comparison between a) a first threshold condition, associated with reduced communication behavior of the patient across a portion of the time period, and b) at least one passive data element of the log of use dataset and the supplementary dataset.

9. The method of claim 1, wherein generating the predictive model includes: at the computing system, implementing a factor analysis approach that models changes in text messaging behavior of the patient across at least a portion of the time period.

10. The method of claim 1, wherein automatically initiating provision of the therapeutic intervention includes enabling a healthcare entity to contact the patient within an application executing at the mobile computing device, thereby preventing the patient from trending toward psychotic episode-risk state.

11. A method for improving psychotic disorder-related state determination for a patient, the method comprising:
    transmitting, from a communication module executing on a mobile communication device to a computing system, a log of use dataset associated with communication behavior of the patient during a time period;
    at the computing system, receiving a mobility sensor supplementary dataset corresponding to a mobility sensor of the mobile communication device, the mobility sensor supplementary dataset characterizing physical activity of the patient during the time period;
    selecting a patient subgroup for the patient from a first subgroup and a second subgroup based on the mobility sensor supplementary dataset, wherein the first subgroup is selected in response to the mobility sensor supplementary dataset indicating a first mobility behavior associated with the first subgroup, wherein the second subgroup is selected in response to the mobility sensor supplementary dataset indicating a second mobility behavior associated with the second subgroup, and wherein selection of the patient subgroup is operable to improve data storage, data retrieval, and the psychotic disorder-related state determination;
    at the computing system, generating a predictive model of a psychotic episode-risk state of the patient associated with at least a portion of the time period, based on the selected patient subgroup and at least one of the log of use dataset and the supplementary dataset; and
    by way of at least one of the computing system and the mobile communication device, initiating provision of a therapeutic intervention for improving a health outcome of the patient, upon detection that a set of parameters outputted from the predictive model of the psychotic episode-risk state satisfy at least one threshold condition.

12. The method of claim 11, further comprising: providing, by way of an application of the mobile communication device, at least one of a set of psychosis-assessment surveys to the patient; and at the computing system, receiving a survey dataset including responses, to at least one of the set of psychosis-assessment surveys, associated with a set of time points of the time period.

13. The method of claim 12, wherein the survey dataset includes responses to a Brief Psychiatric Rating Scale (BPRS)-derived survey and a sleep information survey, and wherein generating the predictive model comprises generating the predictive model from a) the survey dataset and b) a passive dataset including the log of use dataset and the supplementary dataset.

14. The method of claim 11, wherein transmitting the log of use dataset further includes: at the computing system, extracting, from the log of use dataset: a number of incoming text messages and a number of outgoing text messages.

15. The method of claim 14, wherein initiating provision of the therapeutic intervention comprises initiating provision of the therapeutic intervention upon detection that at least one of: a) the number of incoming text messages and b) the number of outgoing text messages is below a threshold number of text messages.

16. The method of claim 11, wherein generating the predictive model includes: at the computing system, implementing an analytical approach that models changes in text messaging behavior of the patient across at least a portion of the time period.

17. The method of claim 16, wherein generating the predictive model includes processing the log of use dataset and the supplementary dataset with a correlation-based feature selection (CFS) algorithm to extract features of the psychotic episode-risk state across the time period.

18. The method of claim 11, wherein generating the predictive model of the psychotic episode-risk state of the patient includes generating an anticipated psychosis-related state of the user at a future time point outside of the time period, and wherein the method further includes automatically initiating provision of a therapeutic intervention for the patient to prevent the anticipated psychosis-related state of the patient.

19. The method of claim 18, wherein the anticipated psychosis-related state is a schizophrenic state, and wherein automatically initiating provision of the therapeutic intervention includes enabling a healthcare entity to contact the patient proximal in time to the future time point.

20. The method of claim 11, wherein initiating provision of the therapeutic intervention comprises rendering the alert at a user interface of a dashboard of a healthcare entity associated with the patient, and wherein rendering the alert further includes providing the healthcare entity with an electronically-implemented tool for contacting the patient.

* * * * *